United States Patent [19]

Lawson et al.

[11] Patent Number: 4,517,188

[45] Date of Patent: May 14, 1985

[54] 1-PYRIMIDINYLOXY-3-HETARYL-ALKYLAMINO-2-PROPANOLS

[75] Inventors: John E. Lawson, Evansville, Ind.; William L. Matier, Libertyville, Ill.; Herbert R. Roth, Evansville, Ind.

[73] Assignee: Mead Johnson & Company, Evansville, Ind.

[21] Appl. No.: 493,124

[22] Filed: May 9, 1983

[51] Int. Cl.$^3$ ................. C07D 239/47; A61K 31/505
[52] U.S. Cl. .................... 514/394; 544/319; 544/320; 544/321; 514/397; 514/398
[58] Field of Search ....... 544/319, 320, 321; 424/251

[56] References Cited

U.S. PATENT DOCUMENTS

| | | | |
|---|---|---|---|
| 3,337,628 | 8/1967 | Crouther | 200/570.7 |
| 4,042,586 | 8/1977 | Wasson | 544/60 |
| 4,139,623 | 2/1979 | Jaeggi | 424/251 |
| 4,193,995 | 3/1980 | Wasson | 424/250 |
| 4,321,398 | 3/1982 | Matier | 544/58 |
| 4,324,788 | 4/1982 | Dorigotti | 424/250 |

FOREIGN PATENT DOCUMENTS 741070  2/1974  South Africa ............ 424/250

OTHER PUBLICATIONS

Antonio et al., J. Med. Chemistry, 21, 123.

*Primary Examiner*—Robert Gerstl
*Attorney, Agent, or Firm*—Richard P. Ryan; Robert H. Uloth

[57] ABSTRACT

1-(4-Pyrimidinyloxy)-3-(hetarylalkylamino)-2-propanols are cardiovascular agents having a range of vasodilator and adrenergic beta-receptor blocking activities making these compounds useful anti-hypertensive agents. Preferred compounds bear a hydrazino or hydrazono substituent in the 2- position of the pyrimidine ring.

36 Claims, No Drawings

1-PYRIMIDINYLOXY-3-HETARYL-ALKYLAMINO-2-PROPANOLS

FIELD OF THE INVENTION

The present invention is concerned with heterocyclic carbon compounds of the pyrimidine series (Class 260/239.75), and with drug bio-affecting and body-treating processes employing these compounds (Class 424/251).

BACKGROUND OF THE INVENTION

A considerable body of prior art exists encompassing compounds of 3-(aryloxy)-2-hydroxypropylamine series which possess beta-adrenergic receptor blocking activity and/or vasodilating properties and are useful in treatment of cardiovascular diseases. Such compounds can be structurally typified by propranolol, chemically, 1-isopropyl-amino-3-(1-naphthoxy)-2-propanol. Propranolol and some related naphthoxypropanolamines are the subject of U.S. Pat. No. 3,337,628 issued Aug. 22, 1967. Numerous subsequent patents have been granted covering carbocyclic ethers in which other aromatic rings or heterocyclic systems replace the naphthoxy group of propranolol. Numerous variations have also been disclosed for the amino substituent of the propanolamine moiety. Reference patents, which are mentioned hereinbelow, generally disclose cardiovascular agents possessing the following generic structure (1):

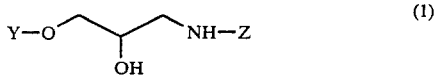

wherein Y is aryl or hetaryl, unsubstituted or substituted; and Z is alkyl, alkylphenyl, or alkylhetaryl.

Matier, et al., in U.S. Pat. No. 4,321,398 issued Mar. 23, 1982, discloses compounds wherein Y is substituted phenyl and Z is an alkylthienyl or alkylbenzothienyl moiety.

Attention is also called to the application Ser. No. 414,748 of Kreighbaum, filed Sept. 3, 1982, which discloses compounds wherein Y is a substituted pyridine system and Z is an alkylindolyl moiety.

Frei, et al., South African Patent Application No. 741070, convention filing data of Feb. 20, 1973, discloses compounds wherein Y is a pyrimidine ring system, either unsubstituted or substituted with a group selected from a long list of possible substituents. Z for this series of compounds can be alkyl or alkylphenyl. No hydrazine or hydrazone substituents on the pyrimidine ring are disclosed in this case.

Jaeggi, et al., U.S. Pat. No. 4,139,623 issued Feb. 13, 1979, also discloses compounds wherein Y is a substituted pyrimidine ring but Z is alkoxyphenyl or alkoxypyrimidine.

Wasson, et al., disclosed subject matter in divisional patents, U.S. Pat. No. 4,042,586 issued Aug. 16, 1977, and U.S. Pat. No. 4,193,995 issued Mar. 18, 1980; relating to compounds in which Z was alkyl, alkylphenyl, or alkylindolyl but Y was a pyrazine ring system.

Similarly, Dorigotti, et al., U.S. Pat. No. 4,324,788 issued Apr. 13, 1982, disclosed compounds wherein Z is alkyl, cycloalkyl, or alkylphenyl but Y is a hydrazone-substituted pyridazine ring system.

These reference patents can be distinguished from the instant invention in view of one or more of the following distinguishing characteristics. Compounds of the instant invention (1) are comprised of a propoxypyrimidine ring structural component, (2) the pyrimidine ring is optimally substituted in the 2-position with a hydrazino or hydrazono moiety, and (3) Z can be alkylthienyl, alkylbenzothienyl, alkylbenzofuranyl, or alkylbenzimidazolyl in addition to alkylindolyl, alkylphenyl, and alkyl.

SUMMARY OF THE INVENTION

This invention concerns a series of cardiovascular agents having vasodilating and beta-adrenergic blocking activities which make them useful as antihypertensive agents. The invention comprises compounds of general formula I and the pharmaceutically acceptable acid addition salts thereof.

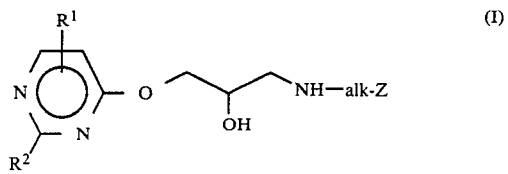

In the foregoing structural formula, $R^1$ can be $C_{1-6}$ alkyl, amino, acylamino, cyano, halogen, or hydrogen; $R^2$ can be amino, alkylcarbonylamino, halogen, hydrazino, hydrazono, hydrogen, or phenyl; alk is $C_{1-6}$ alkylene, either straight chain or branched; and Z is selected from the group consisting of hydrogen, phenyl, indole, thienyl, benzothienyl, benzofuranyl, and benzimidazolyl.

There are two groups of preferred compounds. In the first group (IA) $R^2$ is only hydrazino or hydrazono while in the second group (IB) $R^2$ is hydrogen, amino, $C_{1-4}$ alkylcarbonylamino, cyano, or halogen and Z is only indole, thiophene, benzothiophene, benzofuran, and benzimidazole.

DETAILED DESCRIPTION OF THE INVENTION

The invention includes compounds having the foregoing structural Formula I and the acid addition salts thereof. In formula I, $R^1$ can be alkyl containing from 1 to 6 carbon atoms, either straight chain or branched, amino, $C_{1-4}$ alkylcarbonylamino, cyano, halogen or hydrogen. In preferred compounds, $R^1$ is hydrogen, $C_{1-4}$ alkyl, and halogen, especially bromo. $R^2$ can be amino, $C_{1-4}$ alkylcarbonylamino, halogen, hydrazino, hydrazono, hydrogen, or phenyl, with hydrazino and hydrazono groups being preferred. Hydrazono substituents have the general structure

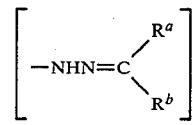

with $R^a$ and $R^b$ being either the same or different and representing $C_{1-3}$ alkyl or phenyl moieties. In Formula I, alk is an alkylene group containing 1–6 carbon atoms, either straight chain or branched, and is preferably t-butyl. Z is selected from the group consisting of hydrogen, phenyl, indole, thienyl, benzothienyl, benzofuranyl, and benzimidazolyl. For preferred compounds, Z is phenyl, indolyl, thienyl, or benzothienyl.

There are two preferred groupings (IA and IB) of the subject compounds. These groups differ as for IA, $R^2$ is either hydrazino or hydrazono while in IB $R^2$ is hydrogen, amino, $C_{1-4}$ alkylcarbonylamino, cyano or halogen but Z is limited to indole, thiophene, benzothiophene, benzofuran, and benzimidazole.

For medicinal use, the pharmaceutically acceptable acid addition salts, those salts in which the anion does not contribute significantly to toxicity or pharmacological activity of the organic cation, are preferred. The acid addition salts are obtained either by reaction of an organic base of structure I with an organic or inorganic acid, preferably by contact in solution, or by any of the standard methods detailed in the literature and available to any practitioner skilled in the art. Examples of useful organic acids are carboxylic acids such as maleic acid, acetic acid, tartaric acid, propionic acid, fumaric acid, isethionic acid, succinic acid, pamoic acid, cyclamic acid, pivalic acid, and the like; useful inorganic acids are hydrohalide acids such as HCl, HBr, HI; sulfuric acid; phosphoric acid; and the like.

It is also to be understood that all the compounds of the present invention embrace all the optical isomer forms, that is, mixtures of enantiomers, e.g., racemic modifications as well as the individual enantiomers and diastereomers. The individual optical isomers of the propanolamine class of compounds of which the instant compounds are members, have most generally been obtained by one of four basic methods. These are: (1) the fractional recrystallization of chiral acid salt derivatives; (2) derivatization with a chiral organic reagent, resolution and regeneration of the original compound in optically active form; (3) synthesis of the single optical isomer using chiral intermediates; and (4) column chromatography utilizing chiral stationary phases. The application of these various methods are well known to practitioners in the art.

Biological testing of the subject compounds of Formula I in animals demonstrates that they possess potent vasodilating properties along with varying degrees of adrenergic beta-receptor blocking properties and intrinsic sympathomimetic activity. Preferred members have a particularly desirable combination in the foregoing actions, and ancillary pharmacological effects, or lack thereof, which particularly suits them for specific cardiovascular indications, e.g. use as antihypertensives. The utility of the compounds of Formula I can be demonstrated in various animal models including antagonism of isoproterenol in the anesthetized dog treated intravenously (adrenergic beta- receptor action), the spontaneous hypertensive and DOCA salt hypertensive rat (antihypertensive action), angiotensin-maintained ganglion-blocked rat model (vasodilator action) and in various other animal and laboratory models (cf: Deitchman, et al., *Journal Pharmacological Methods,* 3, 311–321 (1980)).

For use as antihypertensives, vasodilators, and/or beta- adrenergic blocking agents, therapeutic processes of this invention comprise systemic administration, by both oral and parenteral routes, of an effective, nontoxic amount of a compound of Formula I or a pharmaceutically acceptable acid addition salt thereof. An effective amount is construed to mean a dose which exerts the desired pharmacological activity, such as those stated hereinabove, without undue toxid side effects when administered to a mammal in need of such treatment. Dosage will vary, according to the subject and route of administration selected, with an expected range of about 0.1 mcg to 100 mg/kg body weight for a compound of Formula I or a pharmaceutically acceptable acid addition salt thereof generally providing the desired therapeutic effect.

The basic structure (I) for compounds of the present invention can be assembled by a convenient general process. This process involves the coupling of a X-substituted pyrimidine (IV) with a suitable W-substituted propanol or incipient propanol intermediate (III) followed by hydrolysis and/or aminolysis, if required, with the substituted amino component of the Formula I compound.

General Process

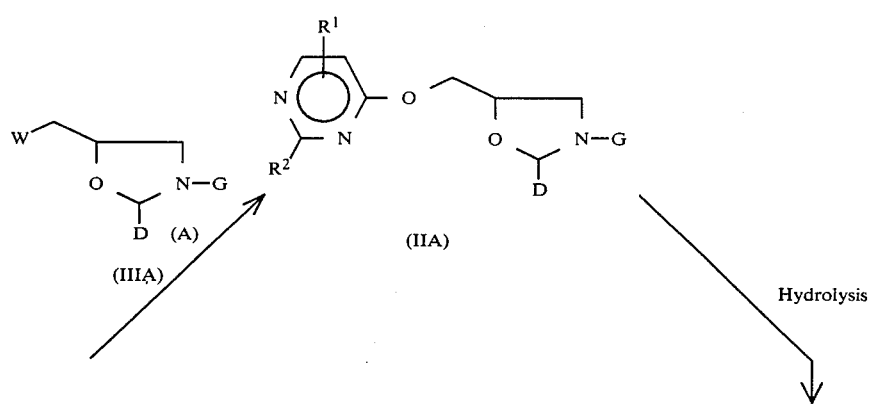

-continued
General Process

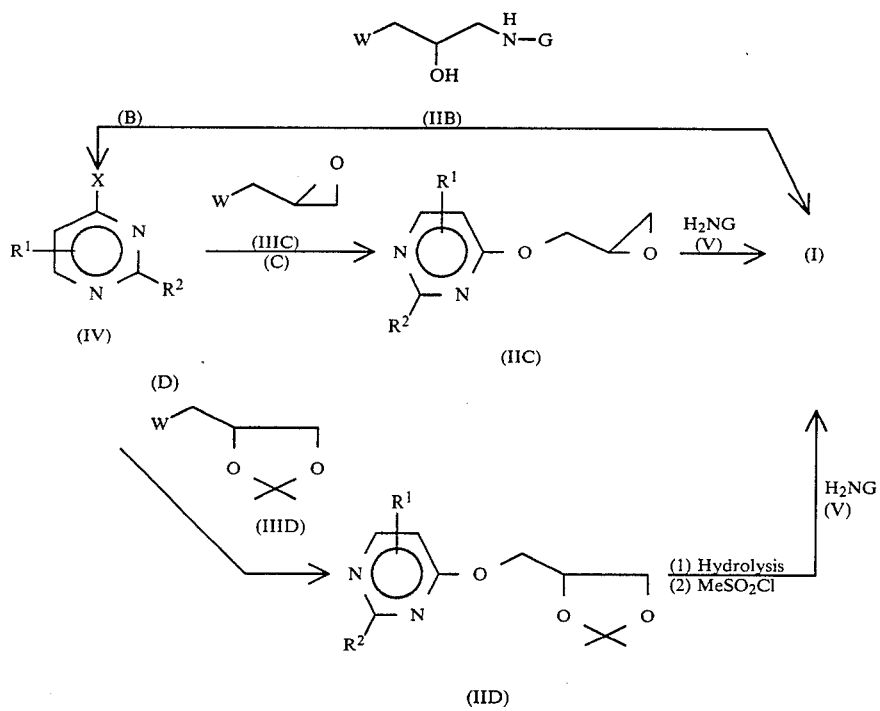

In this general process, as illustrated above, D is hydrogen, or preferably phenyl; G is the radical [-alk-Z]; X is hydroxyl or halogen, preferably chloride; W is halogen, preferably chloride, when X is hydroxyl and is hydroxyl when X is halogen. Generally, the hydroxyl-bearing reactant is initially converted to the oxide anion with a strong base prior to reaction with the halogen-bearing intermediate.

This process employs methods known in the prior art for the preparation of 1-(substituted amino)-3-hetaryloxy)-2-propanols as disclosed in the patents and publications cited in "Background of the Invention" section of this disclosure. Basically, the process involves reaction of the appropriately substituted pyrimidine with either (A) a 3-(G-substituted oxazolidin-5-yl)methanol (or methyl halide) to give IIA, followed by hydrolysis; or (B) a G-substituted aminopropanediol (or halopropanol) of Formula IIB; or (C) glycidol to give IIC, followed by amination with H₂NG; or (D) the cyclic ketal to give IID, followed by hydrolysis, activation of the terminal hydroxy, and aminolysis of H₂NG. Method B is preferred in the above process. The hydrolysis steps in the above general process are usually accomplished with dilute mineral acid of from 0.1N to 1N concentration at temperatures of from about 20°–100° C. The amination reactions of the general process can be carried out simply by heating an amine of the Formula H₂NG with an epoxy ether (IIC) or a propanediol (from IID) either neat or in the presence of a reaction inert organic solvent. No catalyst or condensation agent is required. Suitable reaction temperatures are from about 60°–200° C.

For a better understanding of the pathways comprising the general process, routes A-D are shown below in greater detail.

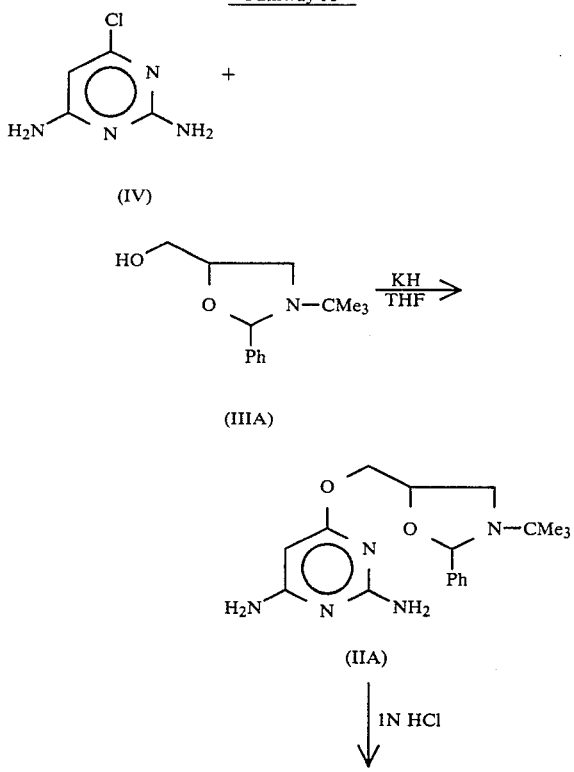

-continued
Pathway A

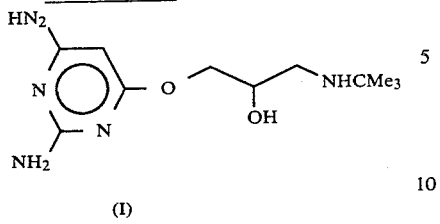

-continued
Pathway C

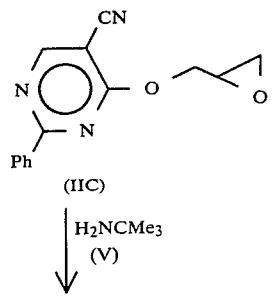

This scheme is carried out by reacting the chloropyrimidine (IV) with the potassium salt of 3-(1,1-dimethylethyl)-2-phenyl-5-oxazolidine-methanol (IIIA) followed by acidic hydrolysis of IIA to provide the corresponding structure I product.

Pathway B

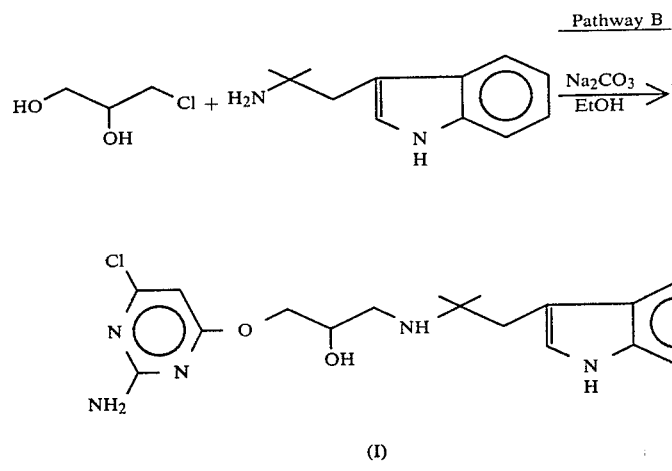

In pathway B, chloropropanediol is treated with an appropriate amine (V) in ethanol. The anion of the resulting aminopropanediol (IIB), prepared using a strong base such as sodium hydride or potassium t-butoxide, was allowed to react with a selected chloro pyrimidine which results in product of structure I.

Pathway C

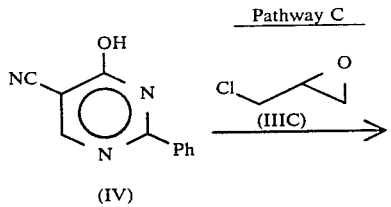

To illustrate pathway C, 4-hydroxy-2-phenyl-5-pyrimidinecarbonitrile is alkylated with epichlorohydrin (IIIC) and the resulting epoxy intermediate (IIC) aminated with t-butylamine (V) to provide the product of structural Formula I.

Pathway D

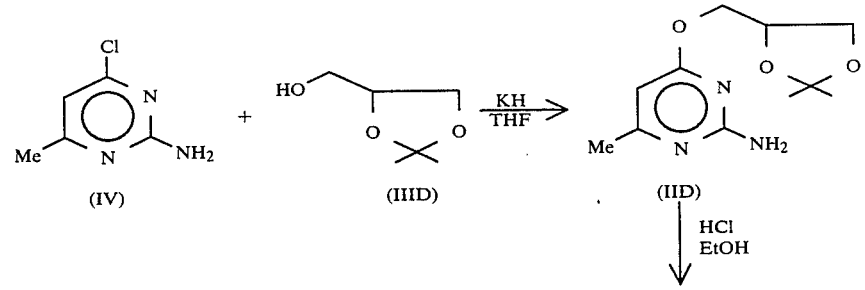

Pathway D

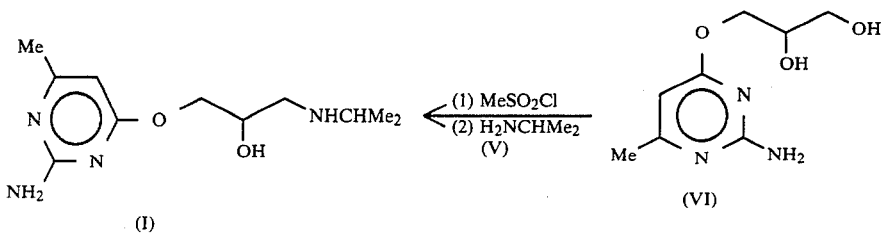

Pathway D involves formation of the anion of solketal (IIID) followed by coupling with a chloropyrimidine (IV). Acid hydrolysis of the pyrmidinyloxy ketal (IID) provides the corresponding pyrimidinyloxy-propanediol (VI). Following activation of the terminal hydroxy group, amination with V gives the structure I product.

The chemical intermediates utilized in the above syntheses are available commercially or may be prepared using standard methods for their preparation as reported in the literature. For example, uracils can be chlorinated conveniently (cf: Mulvey, et al., *J. Heterocycl. Chem.*, 10, 79 (1973); Koppel, et al., *J. Org. Chem.*, 27, 181 (1962) as shown.

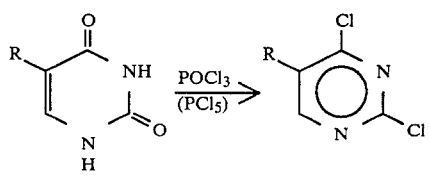

The intermediate heterocyclic alkylaminopropanols (IIB) which are utilized in the preferred synthetic pathway B, are conveniently prepared by reacting an appropriately substituted heterocyclic alkylamine with 3-chloro-1,2-propanediol in refluxing alcohol containing sodium carbonate. This process is illustrated by the reaction shown below which is essentially the first step of pathway B. In this reaction scheme, alk and Z are as defined in Formula I.

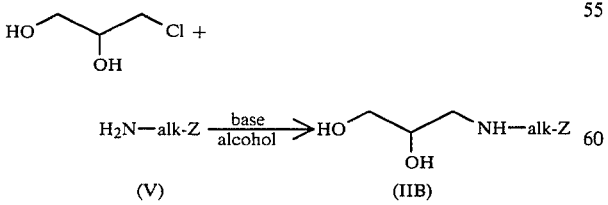

The hydrazino and hydrazono containing compounds of structural Formula I are obtained from Formula I compounds containing a chloro substituent on the pyrimidine ring moiety. These conversions are illustrated in the following scheme.

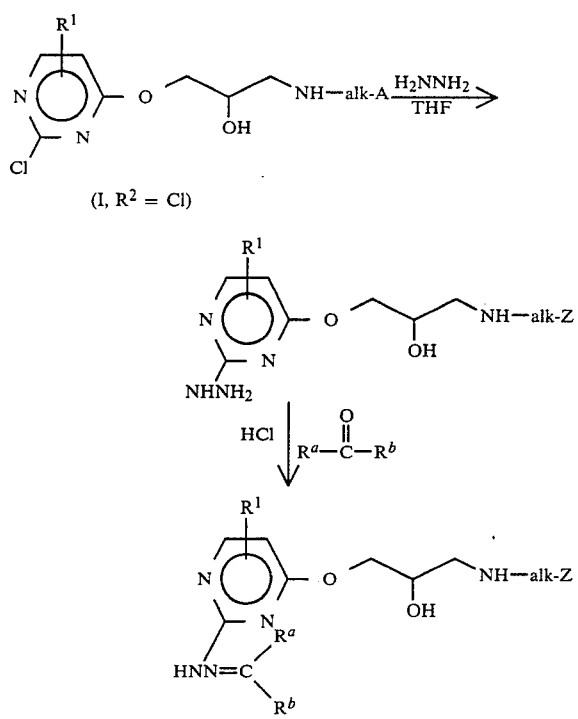

Similarly, compounds of Formula I wherein $R^1$ or $R^2$ is amino can be converted to the corresponding acylamino analogs via straightforward acylation of the amino group.

In summary, it is also an aspect of the present invention to prepare the two preferred groups (IA and IB) of subject compounds by the following processes.

IA COMPOUND PREPARATION

For preparation of a compound of Formula IA

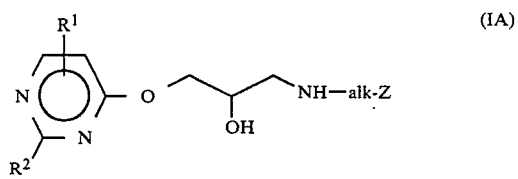

wherein $R^1$ is hydrogen, $C_{1-6}$alkyl, amino, $C_{1-4}$alkylcarbonylamino, cyano or halogen; $R^2$ is —NHNH$_2$ or

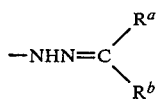

with $R^a$ and $R^b$ being the same or different and representing $C_{1-3}$ alkyl or phenyl; alk is $C_{1-6}$ alkylene, either straight chain or branched; and Z is selected from the group consisting of hydrogen, phenyl, indole, thiophene, benzothiophene, benzofuran, and benzimidazole; the process comprises initial use of one of the following variations (1a–d) beginning with a chloropyrimidine compound of structure IV, $R^2=Cl$ and ending with an intermediate compound of structure IA with $R^2$ being Cl. The four method variations shown as a–d represent optional synthetic pathways which may be selected for the initial step of the process. The process is completed either by introduction of the hydrazine group in Step 2, if the hydrazine product is desired, or with hydrazone formation (Step 3), if a hydrazone product is desired. The total process comprises:

1. Reacting a 2-chloropyrimidine compound of structure IV,

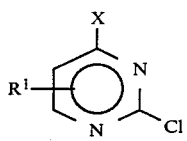

(IV)

wherein $R^1$ is hydrogen, $C_{1-6}$ alkyl, amino, $C_{1-4}$ alkylcarbonylamino, cyano, or halogen; and X is hydroxyl or halogen;

(a) with an oxazolidine of structure IIIA,

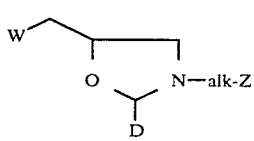

(IIIA)

wherein D is hydrogen or preferably phenyl; -alk and Z are the same as defined hereinabove; and W is halogen, preferably chloride, when X is hydroxyl and W is hydroxyl when X is halogen; to give the intermediate compound of structure IIA,

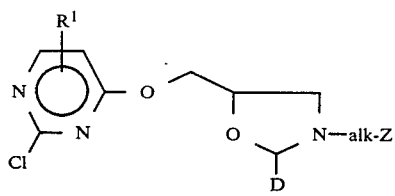

(IIA)

with $R^1$, D, alk, and Z corresponding to IIIA as defined above. Hydrolysis of IIA gives the intermediate compound I

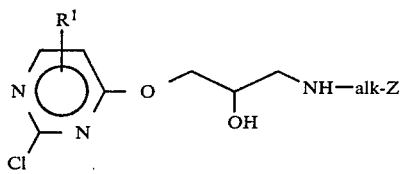

(I: $R^2 = Cl$)

to be used in Step 2.

(b) with an aminopropanediol (or halopropanol) of structure IIB,

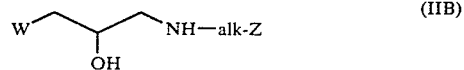

(IIB)

wherein W, alk, and Z are as defined above. This pathway yields the intermediate compound I: R=Cl directly.

(c) with glycidol (IIIC),

(IIIC)

with W as defined above to give the intermediate compound IIC,

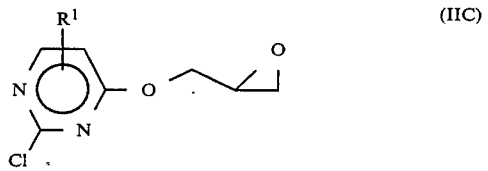

(IIC)

with $R^1$ as defined above. Amination of IIC with V, $$H_2N-alk-Z \qquad (V)$$

wherein alk and Z are as defined above, yields the intermediate I: $R^2=Cl$.

(d) With solketal (IIID)

(IIID)

wherein W is as defined above, to give IID,

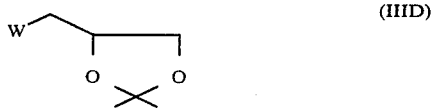

(IID)

wherein $R^1$ is as defined above, followed by hydrolysis to give the pyrimidinyloxypropanediol compound VI,

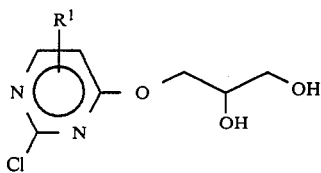

with R¹ as defined above. Treatment of VI with methanesulfonyl chloride to activate the terminal hydroxy group allows ready amination with V to give I: R²=Cl.

2. The intermediate compound of Formula I, prepared in Step 1, is treated with hydrazine to give the 2-hydrazino analog of structure I

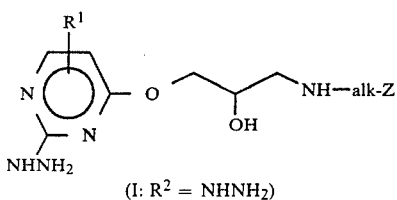

3. If the desired end product is a hydrazone derivative, then the hydrazine derivative obtained in Step 2 is treated with an appropriate carbonyl compound VII

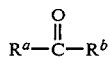

with $R^a$ and $R^b$ the same as defined hereinabove, under acidic conditions to obtain the product of structure

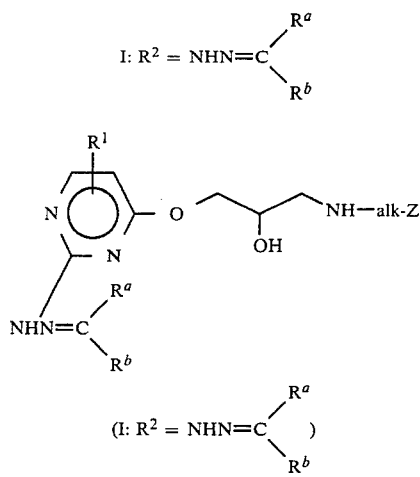

IB COMPOUND PREPARATION

For preparation of a compound of Formula IB

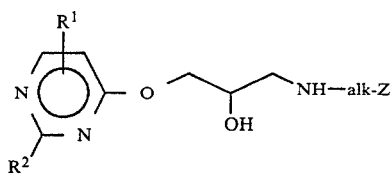

wherein R¹ is hydrogen, $C_{1-6}$ alkyl, amino, $C_{1-4}$ alkylcarbonylamino, cyano, or halogen; R² is hydrogen, amino, $C_{1-4}$ alkylcarbonylamino, halogen, or phenyl; alk is $C_{1-6}$ alkylene, either straight chain or branched; and Z is selected from the group consisting of indole, thiophene, benzothiophene, benzofuran, and benzimidazole; the process comprises selection and use of one of the following variations (a-d).

The IB synthetic process comprises:

Reacting a pyrimidine starting material of structure IV,

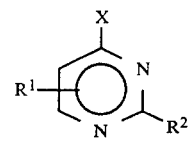

wherein R¹ and R² are the same as defined above for IB; and X is hydroxyl or halogen;

(a) with an oxazolidine of structure IIIA,

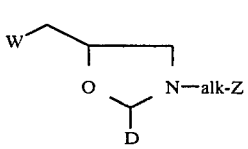

wherein D is hydrogen or preferably phenyl; alk and Z are the same as defined above for IB; and W is halogen, preferably chloride, when X is hydroxyl and W is hydroxyl when X is halogen; to give the intermediate compound of structure IIA,

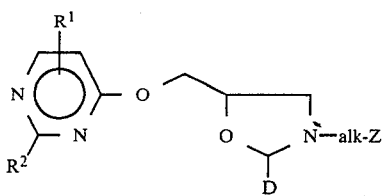

with R¹, R², D, alk, and Z the same as defined hereinabove. Hydrolysis of IIA gives the product compound IB.

(b) With an aminopropanediol (or halopropanolamine) of Formula IIB,

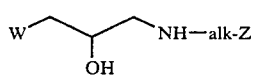

wherein W, alk, and Z are as defined hereinabove; to give the desired IB product.

(c) with glycidol (IIIC),

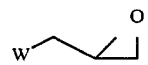

wherein W is as defined above; to give IIC,

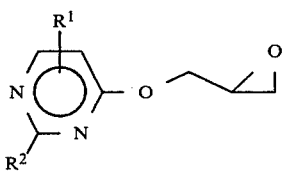

wherein $R^1$ and $R^2$ are as defined above. Amination of IIC with V,

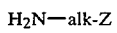

wherein alk and Z are as defined above to give IB.

(d) With solketal (IIID),

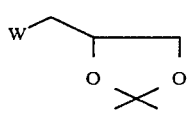

wherein W is as defined above; to give IID,

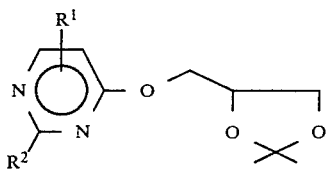

wherein $R^1$ and $R^2$ are as defined above; followed by hydrolysis to give VI,

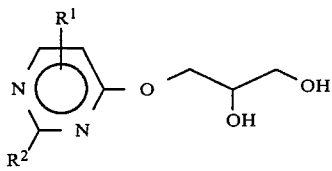

wherein $R^1$ and $R^2$ are as defined above. Treatment of VI with methanesulfonyl chloride activates the terminal hydroxy group allowing facile aminolysis by V to give IB.

The compounds of the present invention can be formulated according to conventional pharmaceutical practice to provide pharmaceutical compositions of unit dosage form comprising, for example, tablets, capsules, powders, granules, emulsions, suspensions, and the like. The solid preparations contain the active ingredient in admixture with non-toxic pharmaceutical excipients such as inert diluents, for example, calcium carbonate, sodium carbonate, lactose, calcium phosphate or sodium phosphate; granulating and disintegrating agents, for example, maize, starch, or alginic acid; binding agents, for example, starch, gelatin or acacia; and lubricating agents, for example, magnesium stearate, stearic acid or talc. The tablets may be uncoated or they may be coated by known techniques so as to defy disintegration at absorption in the gastrointestinal tract and thereby provide a sustained action over a longer period. Liquid preparations suitable for parenteral administration include solutions, suspension, or emulsions of the compounds of Formula I. The aqueous suspensions of the pharmaceutical dosage forms of the compounds of Formula I contain the active ingredient in admixture with one or more non-toxic pharmaceutical excipients known to be suitable in manufacture of aqueous suspensions. Suitable excipients are, for example, suspending agents such as sodium carboxymethylcellulose, methylcellulose, hydroxypropyl methylcellulose, sodium alginate, polyvinylpyrrolidone, gum tragecanth and gum acacia. Suitable disbursing or wetting agents are naturally occuring phosphatides, for example, lecithin, polyoxyethylene stearate.

Non-aqueous suspensions may be formulated by suspending the active ingredient in vegetable oil, for example, olive oil, sesame oil, or coconut oil, or in a mineral oil, for example, liquid parafin. The suspensions may contain a thickening agent such as beeswax, hard paraffin, or cetyl alcohol. Sweetening and flavoring agents generally used in pharmaceutical compositions may also be included such as saccharin, sodium cyclamate, sugar and caramel to provide a palatable oral preparation. The compositions may also contain other absorbing agent, stabilizing agents, wetting agents, and buffers.

DESCRIPTION OF SPECIFIC EMBODIMENTS

The compounds which constitute this invention, their methods of preparation and their biologic actions will appear more fully from a consideration of the following examples and appended claims which are given for the purpose of illustration only and are not to be construed as limiting the invention in sphere or scope. In the following examples, used to illustrate the foregoing synthetic processes, temperatures are expressed in degrees celcius and melting points are uncorrected. The nuclear magnetic resonance (NMR) spectral characteristics refer to chemical shift ($\delta$) expressed as parts per million (ppm) versus tetramethylsilane (TMS) as reference standard. The relative area reported for the various shifts in the H NMR spectral data corresponds to the number of hydrogen atoms of a particular functional type in the molecule. The nature of the shifts as to multiplicity is reported as broad singlet (bs), singlet (s), multiplet (m), or doublet (d). Abbreviations employed are DMSO-$d_6$ (deuterodimethylsulfoxide), CDCl$_3$ (deuterochloroform), and are otherwise conventional. The infrared (IR) spectral descriptions include only absorption wave numbers (cm$^{-1}$) having functional group identification value. The IR determinations were employed using potassium bromide (KBr) as diluent. The elemental analyses are reported as percent by weight.

Synthesis of Intermediates
A. Intermediates of Formula H$_2$N—Alk—Z

EXAMPLE 1

$\alpha,\alpha$-Dimethyl-$\beta$-(thienyl)ethaneamine

A mixture of 57% oil emulsion of sodium hydride (3.1 g, 0.07 mole), tetrahydrofuran (68 mL) and diisopropylamine (6.87 g, 0.07 mole) was stirred under nitrogen atmosphere as isobutyric acid (5.98 g, 0.07 mole) was added dropwise. The mixture was heated at reflux for 15 min to complete formation of the salt. After cooling to 0°, a solution of n-butyllithium in hexane (42 mL of 1.6 molar solution, 0.07 mole) was added in small portions while holding the temperature below 10°. The resulting turbid solution was kept at 0° for 15 min and then warmed to 30°–35° for 30 min. After again cooling to 0°, 2-chloromethylthiophene (9 g, 0.07 mole) was added dropwise over 15–20 min while holding the temperature between 0° and 50°. The mixture was kept at 0° for 30 min, in the range of 30°–35° for 1 hr and was then cooled to 15°. Water (90 mL) was added dropwise and the aqueous layer was separated. The organic phase was washed with a mixture of water (50 mL) and ether (75 mL). The aqueous extracts were combined, washed with ether and then acidified with conc HCl. The oily product was extracted with ether and the combined ether extracts dried (MgSO4). Removal of the ether in vacuo gave 11.4 g (91%) of 2,2-dimethyl-3-(2-thienyl)-propanoic acid of sufficient purity for use.

A solution of 2,2-dimethyl-3-(2-thienyl)propanoic acid (11.2 g, 0.06 mole), diphenylphosphorylazide (16.7 g, 0.06 mole) (Aldrich Chemical Company), and triethylamine (6.14 g, 0.06 mole) in t-butanol (100 mL) was heated at reflux for 5 hrs. The solution was poured into water (300 mL) and the crude material extracted with ether. The combined extracts were washed with brine, dried (MgSO4) and evaporated to 11.9 g of an oil. This oil was added to a mixture of ethylene glycol (50 mL), H2O (20 drops) and KOH (10 g). The mixture was heated at reflux for 5 hr, cooled to 25°, diluted with H2O (300 mL) and acidified to pH 1 with conc HCl. Acid insoluble material was removed by washing with ether. The aqueous solution was then made basic with 50% NaOH solution and the product was extracted with ether. The ether extracts were combined, washed with brine, dried (MgSO4) and concentrated in vacuo to 6.9 g (74%) of product. The NMR spectrum is consistent with the structure of this intermediate compound.

EXAMPLE 2

α,α-Dimethyl-β-(3-benzo{b}thienyl)ethaneamine 2,2-Dimethyl-3-(3-benzo[b]thienyl)propanoic acid was obtained in 82% crude yield from 3-(chloromethyl)benzo{b}thiophene using the procedure for preparation of the corresponding thienyl intermediate as outlined in the first paragraph of Example 1. The yellow viscous oil so obtained exhibited an NMR spectrum consistent with the assigned structure and was sufficiently pure for continued use. Thin layer chromatography on silica plates gave $R_f$=0.7 (ethyl acetate).

Employing this benzothienyl propanoic acid intermediate in a synthetic procedure analogous to that of the second paragraph in Example 1 resulted in a 71% yield of the crude ethaneamine product with an NMR spectrum consistent with the assigned structure and sufficiently pure for use. Thin layer chromatography on silica plates gave $R_f$=0.6 (CHCl3, NH3).

EXAMPLE 3

1,1-Dimethyl-2-(1H-benzimidazol-2-yl)ethylamine

A solution of o-phenylenediamine (5.4 g, 0.05 mole) and 2,2-dimethylsuccinic acid (7.5 g, 0.05 mole) in 50 mL of 4.8 N HCl was refluxed without condenser until the total volume was reduced to about 20 mL. Evaporation at 100° and 40 torr afforded a green paste which was taken up in 100 mL H2O and made alkaline (pH 9) with 20% NaOH. The mixture was filtered removing tarry matter and the clear yellow filtrate was concentrated, cooled and the pH adjusted to about 6 by addition of acetic acid. A light yellow solid precipitated and was isolated by filtration and dried in air to give 9 g of α,α-dimethyl-1H-2-benzimidazolepropanoic acid, m.p. 223°–226° (dec). Recrystallization from acetonitrile-methyl ethyl ketone-methanol (30-30-40) afforded 6.7 g (61%) of colorless needles, m.p. 266°–267° (dec).

A solution containing 11.2 g of this benzimidazolepropanoic acid (0.05 mole), diphenylphosphorylazide (14.0 g, 0.05 mole) and triethylamine (5.0 g, 0.0 mole) in 100 mL of t-butanol was heated at reflux for 10 hr. The volatile material was evaporated at 100° and 30 torr and the residue was diluted with ethanol-methylene chloride. Filtration of the chilled mixture provided a total of 6.5 g of 3,4-dihydro-3,3-dimethylpyrimido{1,6-a}benzimidazol-1(2H)-one as a white solid, m.p. 205°–210°. This material can be purified by reprecipitation from acid solution using 20% NaOH to afford white flakes, m.p. 211°–215°.

A solution of 0.5 g of this cyclic urea (0.0023 mole) and 1.0 g f 35% KOH (0.22 mole) in 95% ethanol (20 mL) was heated at reflux for 8 hr, after which the mixture was boiled to near dryness by removing the condenser. Five mL of isopropyl alcohol and 20 mL of water were added and the mixture was boiled to near dryness again. The crystalline mass obtained by cooling the residue was separated on a Buchner funnel to give 0.4 g of crude product, m.p. 209°–214°. Recrystallization from isopropyl alcohol afforded 250 mg, m.p. 209°–211°.

EXAMPLE 4

2-(2-Amino-2-methylpropyl)indole

A solution of indol-2-carboxylic acid (10.0 g, 0.06 mole) and thionyl chloride (20.0 g, 0.17 mole) in 130 ml of dry ether was stirred for 12–18 hrs at room temperature under nitrogen atmosphere. The reaction mixture was filtered and the filtrate was concentrated to an oily residue which was taken up in 150 mL of dry ether. This ether solution was treated with 80 mL of dimethylamine in 90 mL of ether. The ether was removed by concentration in vacuo and the residue crystallized in isopropyl alcohol. The solid was isolated by filtration to give 4.0 g (34%) of the 2-indolyl amide product, m.p. 181°–183°.

This indolyl amide was dissolved in 100 mL tetrahydrofuran and the resulting solution added dropwise to a stirred suspension comprised of 3 g lithium aluminum hydride in 50 mL of tetrahydrofuran under a nitrogen atmosphere. After being refluxed for 2 hr, the reaction mixture was cooled and decomposed with a small amount of water and dilute sodium hydroxide solution. The resulting mixture was filtered and the filtrate concentrated to a residual oil which was taken up in ethanol and treated with a slight excess of dimethyl sulfate. The resulting alcoholic solution was stirred at room temperature for 4 hr and then concentrated in vacuo to dryness giving as residue the trimethylamine quaternary salt.

The crude quaternary salt product (3.0 g, 0.01 mole) was combined with NaOH (2.0 g pellets, 0.05 mole) and 2-nitropropane (15 mL) and the mixture was heated at reflux under a nitrogen atmosphere for 1 hr. The resultant dark thick mixture was cooled, diluted with water, acidified with acetic acid to a pH of approximately 6 and then extracted with ether. The ether extracts were combined, washed with water, dried (MgSO4) and concentrated to a dark residue which was chromatographed on a silica column and diluted with methylene chloride. Removal of the methylene chloride and recrystallization of the crude material from isopropyl alcohol-water gave 0.4 g of 2-(2-methyl-2-nitropropyl)indole as a cream color solid, m.p. 102°–103°.

Reduction of this nitro product with Raney Nickel and hydrazine in ethanol yields the desired indole alkylamine as a white solid, m.p. 130°-133°.

Additional intermediates of this class can either be obtained commercially, prepared by known procedures in the literature (e.g. 2-(3-indolyl)-1,1-dimethylethylamine is prepared by the method of Snyder, et al., *J. Am. Chem. Soc.*, 69, 3140 (1947) from 3-indolyl-methyldimethylamine (gramine) and 2-nitropropane followed by reduction of resulting 2-(3-indolyl)-1,1-dimethylnitroethane); or by modification of the foregoing synthetic examples. By appropriate utilization of these procedures, intermediates wherein Z is benzofuran or positional isomers of thiophene and benzothiophene can be prepared.

B. Intermediates of Formula II

The class of intermediates designated as II can be prepared according to methods reported in the literature or by following the procedure outlined in the following examples. Structural variation of these intermediates can be obtained by making appropriate modifications which would be evident to those skilled in the art.

EXAMPLE 5

(IIA)

5-{(2,4-Diamino-6-pyrimidinyl)oxy}-3-(1,1-dimethylethyl)-2-phenyloxazolidine 3-(1,1-Dimethylethyl)-2-phenyl-5-oxazolidinemethanol (8.2 g, 0.035 mole, prepared according to the method disclosed in U.S. Pat. No. 3,998,835 issued Dec. 21, 1976 and assigned to Sandoz, Ltd.) was dissolved in tetrahydrofuran (60 mL) and treated dropwise, under nitrogen, with 24% potassium hydride in mineral oil (5.4 g, 0.032 mole). After stirring at 25° for 10 min, the mixture was heated at 45° for 1 hr. 2,4-Diamino-6-chloropyrimidine (4.3 g, 0.03 mole) was added and the mixture heated in a 100 mL stainless steel Parr bomb at 100°-105° for 18 hrs. After cooling, a yellow insoluable gum was collected. The filtrate was concentrated to an oil, from which three crops of solid (m.p. 92°-105°) were isolated by trituration with CCl$_4$ and ether.

EXAMPLE 6

(IIB)

3-{{-2-(3-Indolyl)-1,1-dimethyethyl}amino}-1,2-propanediol Hydrate

A mixture of α,α-dimethyl-β-(3-indolyl)ethaneamine (10.0 g, 0.05 3 mole), Na$_2$CO$_3$ (11.3 g, 0.106 mole), 3-chloro-1,2-propanediol (7.0 g, 0.064 mole) and ethanol (250 mL) was stirred overnight at reflux. After cooling, the mixture was filtered and concentrated in vacuo. The residue was dissolved in ethyl acetate, decolorized (Darco G-60), and evaporated to a volume of 100 mL. The solution deposited a white solid which was recrystallized from ethyl acetate to give 7.7 g (55%), m.p. 112°-114°.

EXAMPLE 7

(IIC)

5-Bromo-2-chloro-4-(oxiranylmethyoxy)pyrimidine

A solution of glycidol (13.0 g, 0.175 mole) and 5-bromo-2,3-dichloropyrimidine (40.0 g, 0.175 mole) in dimethylformamide (350 mL) was added dropwise to a stirring nitrogen-flushed, chilled suspension of sodium hydride (from 10.1 g, 0.21 mole, of NaH washed free of mineral oil) in dimethylformamide (350 mL). Following the addition, the reaction mixture was poured into 1:1 brine-water (4.5 l) and extracted with ethyl acetate (5×750 mL). Combined extracts were washed with water and brine, dried (MgSO$_4$) and concentrated in vacuo to give 44.7 g of an oil which solidified. Trituration of the crude product in isopropyl alcohol-isopropyl ether gave 21.9 g (47%) of product, m.p. 63°-73°.

EXAMPLE 8

(IID)

2-Amino-6-chloro-4-(2,3-dihydroxypropoxy)pyrimidine

Solketal (20.2 g, 0.152 mole) was added dropwise to a suspension of 24.3% potassium hydride in oil (27.6 g, 0.167 mole) in 500 mL of dry tetrahydrofuran. After hydrogen evolution was complete, a solution of 2-amino-4,6-dichloropyrimidine (25 g, 0.152 mole) in 500 mL tetrahydrofuran was added. The mixture was refluxed for 18 hrs and then the tetrahydrofuran was removed in vacuo and the residue extracted with 600 mL of chloroform. The extract was decolorized (Darco G-60), and then filtered. Chilling the filtrate gave 24.3 g (61.4%) of 2-amino-6-chloro-4-{4-(2,2-dimethyl-1,3-dioxalanyl)methoxy}-pyrimidine, m.p. 149°-151°.

Synthesis of Products
Method A

EXAMPLE 9

1{(2,4-Diamino-6-pyrimidinyl)oxy}3-{1,1-dimethylethyl)amino}-2-propanol Dihydrochloride Hydrate The oxazolidine intermediate (IIA, prepared in Example 5) was hydrolyzed by stirring with 40 ml. of 1N HCl at 45°-50° for 1 hr. After cooling, the solution was washed with ether, made basic with 15% NaOH, and extracted with ethyl acetate. The extracts were dried (K$_2$CO$_3$), concentrated in vacuo and the residue dissolved in acetone. The acetone solution was acidified with ethanolic HCl, concentrated, and the residue recrystallized from methanol-isopropyl ether to give 1.4 g (32%), m.p. 221°-223° (dec).

Anal. Calcd. for C$_{11}$H$_{21}$N$_5$O$_2$·2HCl·H$_2$O: C, 38.16; H, 7.28; N, 20.23. Found: C, 38.32; H, 6.92; N, 20.27.

NMR (DMSO-d$_6$): 1.34 (9,s); 3.00 (2,m); 4.28 (3,m); 5.48 (1,s); 8.05 (4,bs); 8.78 (1,bs); 9.34 (1,bs).

IR (KBr): 785, 1130, 1235, 1380. 1440, 1465, 1550, 1650, 2800, and 2970 cm$^{-1}$.

Method B

EXAMPLE 10

1-{(2-Amino-6-chloro-4-pyrimidinyl)oxy}-3-{{3-indolyl)-1,1-(dimethylethyl)}amino}-2-propanol Hydrochloride 3-{2-(3-Indolyl)-1,1-(dimethylethyl)amino}-1,2-propanediol hydrate (IIB, 11.0 g, 0.042 mole) was added to a solution of potassium t-butoxide (4.7 g, 0.042 mole) in dry tetrahydrofuran (275 mL). After the mixture was stirred at reflux for 1.5 hr, a solution of 2-amino-4,6-dichloropyrimidine (6.8 g, 0.042 mole) in tetrahydrofuran (220 mL) was added dropwise in 1 hr. The reaction mixture was stirred at 25° for 6 hrs, allowed to stand overnight, and evaporated to dryness. The residue was slurried in ethyl acetate and water, the organic layers dried (MgSO$_4$) and concentrated to a gummy residue. The gum was triturated in warm dilute hydrochloric acid, filtered, made basic with dilute sodium hydroxide solution and extracted with ethyl acetate. After drying (MgSO$_4$), the ethyl acetate extract was concentrated in vacuo, the residue dissolved in isopropyl alcohol and acidified with ethanolic HCl. The precipitated hydrochloride (7.0 g) was recrystallized twice from methanol-ethyl acetate to afford 4.9 g (27%) product, m.p. 192°–195° (dec).

Anal. Calcd. for C$_{19}$H$_{24}$ClN$_5$O$_2$.HCl: C, 53.53; H, 5.91; N, 16.43. Found: C, 53.81; H, 5.92; N, 16.15.

NMR (DMSO-d$_6$): 1.30 (6,s); 3.05 (4,m); 4.40 (3,m); 6.11 (1,bs); 6.31 (1,s); 7.35 (7,m); 9.00 (1,bs); 9.51 (1,bs); 11.50 (1,bs).

IR (KBr): 750, 1145, 1250, 1330, 1430, 1560, 1580, 1625, 2800, 2980, 3330, and 3400 cm$^{-1}$.

Method C

EXAMPLE 11

1-{(5-Bromo-2-chloro-4-pyrimidinyl)oxy}-3-{{1,1-dimethyl-2-(3-benzothienyl)ethyl}amino}-2-propanol Hydrochloride A solution of 1,1-dimethyl-2-(3-benzothienyl)ethaneamine (8.2 g, 0.04 mole) in absolute ethanol (50 mL) was added dropwise to a stirring suspension of 5-bromo-2-chloro-4-(oxiranylmethoxy)pyrimidine (10.6 g, 0.04 mole) in absolute ethanol (100 mL). The mixture was stirred at reflux for 3 hr and the resulting solution acidified with ethanolic HCl. Recrystallization of the crude product from methanol-isopropyl ether gave 6.9 g (34%) product, m.p. 212°–213° (dec).

Anal. Calcd. for C$_{19}$H$_{21}$BrClN$_3$O$_2$S.HCl: C, 44.95; H, 4.37; N, 8.28. Found: C, 44.73; H, 4.33; N, 8.15.

NMR (DMSO-d$_6$): 1.31 (6,s); 3.42 (4,m); 4.54 (3,m); 6.05 (1,bs); 7.38 (2,m); 7.61 (1,s); 8.02 (2,m); 8.72 (1,s); 9.05 (1,bs); 9.65 (1,bs).

IR (KBr): 730, 765, 1188, 1220, 1335, 1360, 1435, 1557, 2800, and 2980 cm$^{-1}$.

EXAMPLE 12

4-{3-(1,1-Dimethylethyl)amino-2-hydroxypropoxy}-2-phenyl-5-pyrimidinecarbonitrile Hydrochloride A mixture of 4-hydroxy-2-phenyl-5-pyrimidinecarbonitrile (Nishigaki, et al, Chem. Pharm. Bull., 18/5, 1003 (1970); 4.0 g, 0.02 mole) and epichlorohydrin (40.0 g, 0.44 mole) was stirred at 130°–140° for 4 hr. The reaction mixture was concentrated to an oil and the toluene soluble portion taken to dryness. Absolute ethanol (40 mL) and t-butylamine (40 mL) were added to the residue and the solution stirred at reflux for 6 hr. Unreaction epichlorohydrin and ethanol were removed by concentration in vacuo. Toluene was added twice to the residue and removed in vacuo. Water (100 mL) was added and insoluble material separated by filtration. The filtrate was made basic with 1N NaOH and the precipitate dissolved in ether. This ether solution was dried (MgSO$_4$) and acidified with ethanolic HCl to afford the product hydrochloride salt. Two recrystallizations from methanol-acetone gave 0.6 g (12%) of product, m.p. 191°–193° (dec).

Method D

EXAMPLE 13

1-(2-Amino-4-chloropyrimidin-6-yl)-oxy-3-{(1-methylethyl)amino}-2-propanol

To a solution of 2-amino-6-chloro-4-{4-(2,2-dimethyl-1,3-dioxalanyl)methoxy}pyrimidine (IID, Example 8, 22 g) in 95% ethanol (600 mL) was added conc HCl to bring the solution of pH 1 (moistened Hydrion B paper). The solution was heated at 60° in a water bath for 1.5 hr.

After cooling to 25°, 20% NaOH solution was added to neutralize the HCl and the ethanol was removed in vacuo. The residue was slurried in H$_2$O (100 mL), the solid filtered and recrystallized from ethanol to give 11.8 g (62.5%) of 2-amino-6-chloro-4-(2,3-dihydroxypropoxy)-pyrimidine, m.p. 175°–177°.

A 10.7 g portion (0.049 mole) of 2-amino-6-chloro-4-(2,3-dihydroxypropoxy)pyrimidine was dissolved in 50 mL pyridine with heating. The pyridine solution was chilled in an ice bath and methanesulfonylchloride (5.5 g, 0.049 mole) was added dropwise while keeping the temperature below 10°. The solution was kept below 10° for 15 min, then a solution of isopropylamine (100 mL) and absolute ethanol (100 mL) were added. After 18 hrs at reflux, the solvent and excess amine were removed in vacuo. Water (approximately 100 mL) was added to the residue, followed by 50% NaOH solution making the pH 11. This basic mixture was extracted with ether; the ether extracts combined and dried (MgSO$_4$) and then concentrated in vacuo to a partially crystallized yellow oil. Recrystallization of this material first from ethyl acetate and then from acetonitrile-isopropyl alcohol gave 2.15 g (17%) of product, m.p. 166°–168°.

Anal. Calcd. for C$_{10}$H$_{17}$ClN$_4$O$_2$: C, 46.07; H, 6.57; N, 21.49. Found: C, 46.32; H, 6.52; N, 21.18.

NMR (DMSO-d$_6$): 1.00 (6,d, 6.0 Hz); 2.66 (3,m); 3.88 (2,m); 4.29 (2,d, 5.9 Hz); 4.72 (1,bs); 6.25 (7.21 (2,bs).

IR (KBr): 795, 1010, 1140, 1250, 1305, 1340, 1445, 1570, 1600, 1650, 2980, 3200, and 3360 cm$^{-1}$.

Hydrazine/Hydrazone Products

EXAMPLE 14

1-{(5-Bromo-2-hydrazino-4-pyrimidinyl)oxy}-3-{{1,1-dimethyl-2-(3-benzothienyl)ethyl}amino}-2-propanol Hydrazine (2.3 g, 0.071 mole) was added dropwise to a stirred suspension of the substituted chloropyrimidine product prepared in Example 11 (6.0 g, 0.12 mole) in tetrahydrofuran (60 mL). The mixture was vigorously stirred under nitrogen for 16 hr. Excess hydrazine in the form of a bottom layer was removed by pipette and the tetrahydrofuran solution constituting the upper layer was decolorized (Darco) and concentrated in vacuo. The residual oil was dissolved in isopropyl alcohol and crystallization induced by scratching. Filtration provided 4.8 g (80%) of product, m.p. 141°–143.5° (dec).

Anal. Calcd. for C$_{19}$H$_{24}$BrN$_5$O$_2$S: C, 48.93; H, 5.19; N, 15.02. Found: C, 48.75; H, 5.21 N, 14.82.

NMR (DMSO-d$_6$): 1.02 (6,s); 2.75 (2,m); 2.90 (2,s); 4.00 (4,m); 4.36 (2d, 5.8 Hz); 4.92 (1,bs); 7.31 (2,m); 7.42 (1,s); 7.89 (2,m); 8.15 (1,s); 8.26 (1,bs).

IR (KBr): 730, 765, 1235, 1285, 1425, 1580, and 2960 cm$^{-1}$.

EXAMPLE 15

1-{{5-Bromo-2-{2-(1-methylethylidene)hydrazino}4-pyrimidinyl}oxy}-3-{{1,1-dimethyl-2-(3-benzothienyl)ethyl}amino}-2-propanol Dihydrochloride The hydrazino pyrimidine compound prepared in Example 14 (1.6 g, 3.4 mmole) was suspended in isopropyl alcohol (15 mL), acidified with ethanolic HCl, and warmed while adding acetone (3 mL). Crystalline dihydrochloride separated from the hot solution. The mixture was filtered to provide 1.9 g (94%) of analytically pure product, m.p. 197°–199° (dec).

Anal. Calcd. for C$_{22}$H$_{28}$BrN$_5$O$_2$S.2HCl: C, 45.60; H, 5.22; N, 12.09. Found: C, 45.27; H, 5.27, N, 11.95.

NMR (DMSO-d₆): 1.31 (6,s); 2.10 (6,s); 3.28 (2,m); 3.45 (2,m); 4.60 (3,m); 7.37 (2,m); 7.60 (1,s); 8.02 (2,m); 8.44 (1,s); 9.30 (1,bs); 9.95 (1,bs).

IR (KBr): 760, 1110, 1160, 1425, 1478, 1610, 1640, 2800, and 2980 cm$^{-1}$.

Additional product I compounds can be prepared using methods contained in the foregoing examples. A tabulation of some selected additional compounds of Formula I appears in Table 1.

compounds. The animals are then dosed again and pressure determinations made 2 and 4 hours later. Heart rate is determined with each pressure measurement as well. A fall in blood pressure at 2 or 4 hours after the second dose in the range of 19–24 mmHg is considered "questionable". "Active" and "inactive" designations are decreases greater and less than the range.

EXAMPLE 46

TABLE 1
Pyrimidinyloxypropanolamines

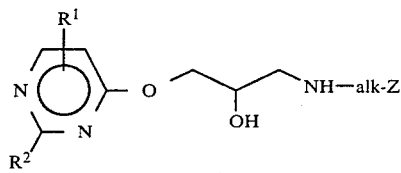

| Example No. | R¹ | R² | alk | Z | m.p. °C. |
|---|---|---|---|---|---|
| 16 | 6-Cl | NH₂ | C(CH₃)₂CH₂ | H | 171–172 |
| 17 | 6-Me | NH₂ | C(CH₃)₂CH₂ | H | 202.5–204.5 |
| 18 | H | Cl | C(CH₃)₂CH₂ | H | 128–143 |
| 19 | 6-Br | $\underset{CH_3CNH}{\overset{O}{\|}}$ | CHCH₃CH₂ | 2-benzofuranyl | — |
| 20 | 5-Me | NHN=C(CH₃)CH₂CH₃ | CH₂CH₂ | 3-benzofuranyl | — |
| 21 | H | NHNH₂ | C(CH₃)₂CH₂ | H | 207–208 (dec) |
| 22 | H | Cl | C(CH₃)₂CH₂ | 3-indolyl | 213–215 |
| 23 | H | NHNH₂ | C(CH₃)₂CH₂ | 3-indolyl | 141–146 (dec) |
| 24 | 6-Me | NHNH₂ | CHCH₃CH₂ | 2-indolyl | — |
| 25 | 6-Br | NHN=C(CH₃Ph | CHCH₃CH₂ | 2-benzimidazolyl | — |
| 26 | H | Cl | C(CH₃)₂CH₂ | 2-thienyl | 156.5–158.5 |
| 27 | H | Cl | C(CH₃)₂CH₂ | phenyl | 165–170 |
| 28 | H | NHNH₂ | C(CH₃)₂CH₂ | phenyl | 117–120 |
| 29 | H | NHNH₂ | C(CH₃)₂CH₂ | 2-thienyl | 86–110 |
| 30 | H | NHN=C(CH₃)₂ | C(CH₃)₂CH₂ | 2-thienyl | 203–205 (dec) |
| 31 | H | NHN=C(CH₃)₂ | C(CH₃)₂CH₂ | phenyl | 206–208 (dec) |
| 32 | H | NHNH₂ | C(CH₃)₂CH₂ | 3-benzothienyl | 125–130 |
| 33 | 6-Et | $\underset{CH_3CNH}{\overset{O}{\|}}$ | CHCH₃CH₂ | 2-benzothienyl | — |
| 34 | H | Cl | C(CH₃)₂CH₂ | 3-benzothienyl | 208–209 (dec) |
| 35 | 5-Br | Cl | C(CH₃)₂CH₂ | H | 172–174 |
| 36 | 5-Br | NHN=C(CH₃)₂ | C(CH₃)₂CH₂ | H | 200–202 (dec) |
| 37 | 5-Br | NHN=C(CH₃)₂ | C(CH₃)₂CH₂ | 2-thienyl | 202–203.5 (dec) |
| 38 | H | NHN=C(CH₃)₂ | C(CH₃)₂CH₂ | 3-thienyl | 188–190 |
| 39 | 5-Br | NHN=C(CH₃)₂ | C(CH₃)₂CH₂ | 3-thienyl | 210.5–202.5 (dec) |
| 40 | 5-CH₃ | NHN=C(CH₃)₂ | C(CH₃)₂CH₂ | 2-thienyl | 208–209 (dec) |
| 41 | 5-CH₃ | NHN=C(CH₃)₂ | C(CH₃)₂CH₂ | H | 217–219 |
| 42 | 5-CH₃ | NHN=C(CH₃)₂ | C(CH₃)₂CH₂ | phenyl | 202–203 |
| 43 | 5-CH₃ | NHN=C(CH₃)₂ | C(CH₃)₂CH₂ | 3-thienyl | 199–201 |
| 44 | $\underset{6-CH_3CNH}{\overset{O}{\|}}$ | NHN=CCH₃Ph | CHCH₃CH₂ | 2-indolyl | — |

BIOLOGICAL EVALUATION

These biological tests were used to gauge the antihypertensive profile of a number of the compounds of Formula I as vasodilators with a range of beta-adrenergic blocking activity.

EXAMPLE 45

The efficacy of antihypertensive agents other than adrenergic beta-receptor blocking agents is commonly estimated in the spontaneous hypertensive rat. Blood pressure values are determined for test animals prior to and 22 hours after oral doses of 30–100 mg/kg of test The angiotensin-maintained ganglion-blocked rat model is utilized as a screening test for estimation of the vasodilator component of activity. Percentage changes in blood pressure in anesthetized rats 30 minutes after intravenous dosing are determined. The intravenous dosing is done with test compounds at 3 mg/kg. Borderline activity is defined as approximately a 10% decrease in blood pressure measured 30 minutes after dosing. "Active" and "inactive" designations are increases greater and less than that.

EXAMPLE 47

Diastolic blood pressure and heart rate responses to a fixed challenge dose of isoproterenol are obtained before and 15 minutes after graded doses to test compound administered intravenously over a 3 minute interval to anesthetized dogs. A branch of a femoral artery and vein are cannulated to record blood pressure and to administer the drugs which are dissolved in saline. The vagi were sectioned bilaterally in the mid-cervical region of the neck and the dogs are ventilated mechanically (Harvard respiratory) with room air at a rate of 20/minute and a stroke volume of 20mL/kg. Heart rate is monitored with a cardiotachometer triggered by the pressure pulse. All measurements are recorded on a Beckman R-612 recorder. The drug effect is expressed in terms of a cumulative dose (microgram/kg) causing 50% inhibition of isoproterenol response.

EXAMPLE 48

Rats (male Wistar) are anesthetized with a combination of urethane and chloralase intraperitoneally. Following induction of anesthesia, chlorisondamine is injected into the peritoneal cavity to produce ganglion blockage. A femoral artery was cannulated to monitor blood pressure and heart rate and two femoral veins were cannulated to administer compounds. The trachea ws intubated and rats were allowed to breath spontaneously. Animals were challenged before and 15 minutes after intravenous administration of test compound with graded doses of isoproterenol and the changes in heart rate recorded. Data were plotted to obtain dose-response curves and the dose of isoproterenol required to elicit a 50 beat per minute ($ED_{50}$) increase in heart rate was interpolated from the curves. Dose shifts are calculated by dividing the $ED_{50}$ after drug by the $ED_{50}$ before drug.

What is claimed is:

1. A pyrimidine compound of Formula IA

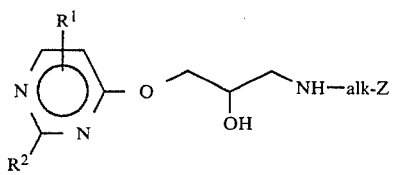

(IA)

or a pharmaceutically acceptable salt thereof wherein
$R^1$ is hydrogen, $C_{1-6}$ alkyl, amino, $C_{1-4}$ alkylcarbonylamino, cyano, or halogen;
$R^2$ is —$NHNH_2$ or

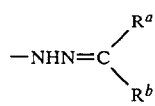

with $R^a$ and $R^b$ being the same or different and representing $C_{1-3}$ alkyl or phenyl;
alk is $C_{1-6}$ alkylene, either straight chain or branched; and
Z is selected from the group consisting of hydrogen, phenyl, indole, thiophene, benzothiophene, benzofuran, and benzimidazole.

2. The pyrimidine compound of claim 1 wherein $R^1$ is hydrogen, $C_{1-4}$ alkyl, and halogen; $R^a$ and $R^b$ are methyl; alk is t-butyl and Z is phenyl, indolyl, thienyl, or benzothienyl.

3. The pyrimidine compound of claim 2 wherein $R^1$ is 5-bromo or 5-methyl.

4. A pyrimidine compound of Formula IB

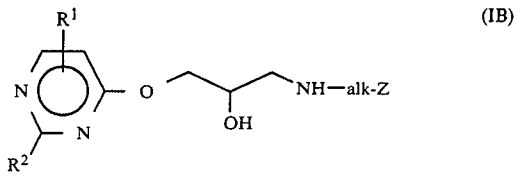

(IB)

or a pharmaceutically acceptable salt thereof wherein
$R^1$ is hydrogen, $C_{1-6}$ alkyl, amino, $C_{1-4}$ alkylcarbonylamino, cyano, or halogen;
$R^2$ is hydrogen, amino, $C_{1-4}$ alkylcarbonylamino, halogen, or phenyl;
alk is $C_{1-6}$ alkylene, either straight chain or branched; and
Z is selected from the group consisting of indole, thiophene, benzothiphene, benzofuran, and benzimidazole.

5. The antihypertensive method which comprises administering to a mammalian host having hypertension a non-toxic antihypertensive effective dose of a compound claimed in claim 1 or claim 4.

6. A pharmaceutical composition in dosage unit form suitable for systemic administration to a mammalian host comprising a phamaceutical carrier and an amount of a Formula I compound of claim 1 or claim 4 to provide an effective non-toxic dose of from 0.1 mcg to 100 mg/kg body weight of said host.

7. The compound of claim 1, 1-[(1,1-dimethylethyl)amino]-3-[(2-hydrazino-4-pyrimidinyl)oxy]-2-propanol.

8. The compound of claim 1, 1-[(2-hydrazino-4-pyrimidinyl)-oxy]-3-[[2-(1H-indol-3-yl)-1,1-dimethylethyl]amino]-2-propanol.

9. The compound of claim 1, 1-[(1,1-dimethyl-2-phenylethyl)-amino]-3-[(2-hydrazino-4-pyrimidinyl)oxy]-2-propanol.

10. The compound of claim 1, 1-[[1,1-dimethyl-2-(2-thienyl)-ethyl[amino[-3-](2-hydrazino-4-pyrimidinyl)oxy]-2-propanol.

11. The compound of claim 1, 1-[[1,1-dimethyl-2-(2-thienyl)-ethyl]amino]-3-[[2-[2-(1-methylethylidene)hydrazino]pyridimin-4-yl]oxy]-2-propanol.

12. The compound of claim 1, 1-[(1,1-dimethyl-2-phenylethyl)-amino]-3-[[2-[2-(1-methylethylidene)hydrazino]pyrimidin-4-yl]oxy]-2-propanol.

13. The compound of claim 1, 1-[[1,1-dimethyl-2-(3-benzothienyl)ethyl]amino-3-[(2-hydrazino-4-pyrimidinyl)oxy]-2-propanol.

14. The compound of claim 1, 1-[(5-bromo-2-hydrazino-4-pyrimidinyl)oxy]-3-[[1,1-dimethyl-2-(3-benzothienyl)ethyl]amino]-2-propanol.

15. The compound of claim 1, 1-[[5-bromo-2-[2-(1-methyethylidene)hydrazino]pyrimidin-4-yl]oxy-]3-[[1,1-dimethyl-2-(3-benzothienyl)ethyl]amino]-2-propanol.

16. The compound of claim 1, 1-[[5bromo-2[2-(1-methylethylidene)hydrazino]pyrimidin-4-yl]oxy]-3-[(1,1-dimethylethyl)amino]-2-propanol.

17. The compound of claim 1, 1-[[5-bromo-2[2(1-methylethylidene)hydrazino]pyrimidin-4-yl]oxy]-3-[[1,1-dimethyl-2-(2-thienyl)ethyl amino]-2-propanol.

18. The compound of claim 1, 1-[[1,1-dimethyl-2-(3-thienyl)-ethyl]amino]-3-[[2-[2-(1-methylethylidene)hydrazino]pyrimidin-4-yl]-oxy]-2-propanol.

19. The compound of claim 1, 1-[[5-bromo-2-[2-(1-methylethylidene)hydrazino]pyrimidin-4-yl]oxy]3-[[1,1-dimethyl-2-(3-thienyl)ethyl]amino[-2-propanol.

20. The compound of claim 1, 1-[[1,1-dimethyl-2-(2-thienyl)ethyl]amino]3-[[5-methyl-2-[2-(1-methylethylidene)hydrazino]-pyridimin-4-yl]oxy]-2-propanol.

21. The compound of claim 1, 1-[(1,1-dimethylethyl)amino]-3-[[5-methyl-2-[2-(1-methylethylidene)hydrazino]pyrimidin-4-yl]oxy]-2-propanol.

22. The compound the claim 1, 1-8 (1,1-dimethyl-2-phenyl-ethyl) amino]-3-[[5-methyl-2-[2-(1-methylethylidene)hydrazino]pyridimidin-4-yl]oxy]-2-propanol.

23. The compound of claim 1, 1-[[1,1-dimethyl-2-(3-thienyl)-ethyl]amino]-3-[[5-methyl-2-[2-methylethylidene)hydrazino]-pyrimidin-4-yl]oxy]-2-propanol.

24. The compound of claim 4, 4-[3-(1,1-dimethylethyl)amino-2-hydroxypropoxy]2-phenyl-5-pyrimidinecarbonitrile.

25. The compound of claim 4, 1-[(2-amino-4-chloropyrimidin-6-yl)oxy]-3-[(1,1-dimethylethyl)amino]-2-propanol.

26. The compound of claim 4, 1-[(2-amino-4-chloropyrimidin-6-yl)oxy]-3-[[(2-(3-indolyl)-1,1-dimethylethyl]amino]-2-propanol.

27. The compound of claim 4, 1-[(2-amino-4-chloropyrimidin-6-yl)oxy]-3-[(1-methylethyl)amino]-2-propanol.

28. The compound of claim 4, 1-[(2-amino-4-methylpyrimidin-6-yl)oxy]-3-[(1-methylethyl)amino]-2-propanol.

29. The compound of claim 4, 1-[2,4-diaminopyrimidin-6-yl)-oxy]-3-[(1,1-dimethylethyl)amino]-2-propanol.

30. The compound of claim 4, 1-[(2-chloro-4-pyrimidinyl)-oxy]-3-[(1,1-dimethylethyl)amino]-2-propanol.

31. The compound of claim 4, 1-[(2-chloro-4-pyrimidinyl)oxy[-3-[[(1,1-dimethyl-2(1H-indol-3-yl)ethyl]amino]-2-propanol.

32. The compound of claim 4, 1-[(2-chloro-4-pyrimidinyl)-oxy]-3-[[1,-dimethyl-2-(2-thienyl)ethyl]amino]-2-propanol.

33. The compound of claim 4, 1-[(2-chloro-4-pyrimidinyl)-oxy]-3-[(1,1-dimethyl-2-phenylethyl)amino]-2-propanol.

34. The compound of claim 4, 1-[(2-chloro-4-pyrimidininyl)-oxy]-3-[[1,1-dimethyl-2-(3-benzothieny)ethyl)ethyl]amino]-2-propanol.

35. The compound of claim 4, 1-[(5-bromo-2-chloro-4-pyrimidinyl)oxy]-3-[[1,1-dimethyl-2-(3-benzothienyl)ethyl]amino]-2-propanol.

36. The compound of claim 4, 1-[(5-bromo-2-chloro-4-pyrimidinyl)oxy]-3-[(1,1-dimethylethyl)amino]-2-propanol.

* * * * *